United States Patent [19]
Lang et al.

[11] Patent Number: 4,504,644
[45] Date of Patent: Mar. 12, 1985

[54] PROTEIN DERIVATIVE CONTAINING GRAFTED ULTRAVIOLET-ABSORBING RADICALS, THE PROCESS FOR ITS PREPARATION AND COMPOSITION IN WHICH IT IS PRESENT

[75] Inventors: Gérard Lang, Saint Gratien; Alain Malaval, Marly la Ville, both of France

[73] Assignee: L'Oreal, Paris, France

[21] Appl. No.: 523,771

[22] Filed: Aug. 16, 1983

[30] Foreign Application Priority Data

Aug. 23, 1982 [FR] France ................................. 82 14480
Jun. 28, 1983 [FR] France ................................. 83 10654
Jun. 28, 1983 [FR] France ................................. 83 10655

[51] Int. Cl.³ .......................... C07G 7/00; A61K 7/42
[52] U.S. Cl. .................................... 527/201; 527/202; 527/102; 424/59; 424/60; 51/972; 424/DIG. 1; 260/112 R; 260/117; 260/119; 260/121; 260/123.5; 260/123.7; 252/89.1, 514/972

[58] Field of Search ............... 527/102, 201, 202, 203; 260/112 R, 117, 119, 121, 123.5, 123.7; 424/59, 60, 78, 174, DIG. 1, 71, 47; 252/89.1

[56] References Cited

U.S. PATENT DOCUMENTS 3,583,855  6/1971  Bolinger et al. ..................... 527/102
4,229,326 10/1980  Morin et al. ......................... 527/102
4,233,430 11/1980  Jacquet et al. ........................ 424/60
4,416,868 11/1983  Vanlerberghe et al. ............... 424/60

Primary Examiner—John Kight
Assistant Examiner—Nathan M. Nutter
Attorney, Agent, or Firm—Cushman, Darby & Cushman

[57] ABSTRACT

The invention describes a protein derivative which has a molecular weight of 500 to 50,000 and has been chemically modified by grafting onto the protein chain radicals which absorb ultraviolet radiation. Also described are a process for the preparation of this protein derivative and compositions, containing this derivative as the active substance, for treating and protecting the skin and hair against photochemical degradation.

27 Claims, No Drawings

PROTEIN DERIVATIVE CONTAINING GRAFTED ULTRAVIOLET-ABSORBING RADICALS, THE PROCESS FOR ITS PREPARATION AND COMPOSITION IN WHICH IT IS PRESENT

The present invention relates to a protein derivative which has been chemically modified by grafting onto the protein chain radicals absorbing ultraviolet radiation. The invention also relates to a process for the preparation of this protein derivative and to compositions, containing this derivative as the active substance, for treating and protecting the skin and hair against photochemical degradation.

A large number of protein hydrolysates are already known which possess valuable cosmetic properties for treating the skin or hair. Furthermore, it is known to graft, onto synthetic polymer chains, radicals of molecules having a filter effect towards ultraviolet radiation; these graft synthetic polymers can be used to prepare cosmetic compositions which filter out the solar radiation harmful to the skin; however, it has been found that these polymers are generally sparingly soluble in the customary cosmetic solvents, that they form films of excessively rigid texture and that they frequently possess a relatively low capacity to absorb UV radiation, which means that they must be included at a high concentration in the compositions in which they are present.

The aim of the present invention is to provide a chemically treated protein derivative which can be used simultaneously as a product for treating and as a product for protecting the skin against the adverse effects of ultraviolet radiation. This product uses a natural polymer chain as a carrier for the grafting on of molecules which filter out the UV radiation. Its use on the skin and hair therefore offers the dual advantage of a treatment effect due to the presence of the protein chains and a protective effect due to the presence of the grafted molecules. Moreover, the protective films which can be formed on the skin have a satisfactory flexibility, so that it is more pleasant to use the compositions in which these products are present than the solar protection compositions containing the grafted synthetic polymers. For the same percentage of UV filter, an increase in the protection factor of the filtering protein is observed, compared with the filter used by itself. These filtering proteins also have a very high chemical resistance in the customary cosmetic media.

The present invention provides a chemically modified protein derivative, characterised in that it has a molecular weight of between about 500 and 50,000 and in that it corresponds to the following general formula:

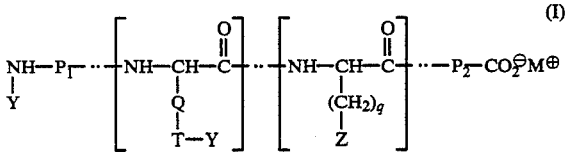

in which formula Y is a radical of a molecule absorbing ultraviolet radiation;

$P_1$ and $P_2$ are radicals of the protein derivative which are not acylated and not chemically modified by nucleophilic addition or substitution;

$M^{\oplus}$ represents $H^{\oplus}$, a cation derived from an alkali metal or from magnesium, or $N^{\oplus}(R_2)_4$, in which formula the radicals $R_2$ are identical or different and represent a hydrogen atom or an alkyl or hydroxyalkyl radical—having at most 4 carbon atoms;

Q is an alkyl, aryl or aralkyl radical of the constituent aminoacids of the protein;

T represents O, NH or, if the protein contains cysteine, S;

Z is:
a radical $SO_3^{\ominus}M^{\oplus}$, the cation $M^{\oplus}$ having the same meaning as above; or
$SR_3$, in which formula $R_3$ represents:

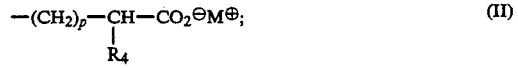 (II)

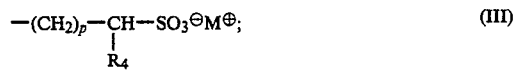 (III)

 (IV)

in which formulae p is an integer between 0 and 5 (inclusive), $R_4$ is a hydrogen atom or an alkyl radical having at most 4 carbon atoms and $R_5$ represents:

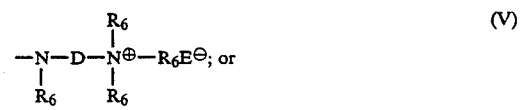 (V)

 (VI)

in which formulae D is a linear or branched alkylene group containing a total of from 2 to 10 carbon atoms, the cation $M^{\oplus}$ having the same meaning as above, the radicals $R_6$ being identical or different and representing a hydrogen atom or an alkyl or hydroxyalkyl radical having at most 4 carbon atoms, and $E^{\ominus}$ being a halide ion or $RCOO^{\ominus}$, $RSO_3^{\ominus}$ or $RSO_4^{\ominus}$, R representing a hydrocarbon rest containing from 1 to 10 carbon atoms; or alternatively an amino radical originating from a basic aminoacid of the protein, monosubstituted or disubstituted by a radical $R_3$, $R_3$ having the same meaning as above;

q is an integer between 1 and 5 (inclusive), except that, if Z represents a radical $SO_3^{\ominus}M^{61}$ or $SR_3$, q is necessarily equal to 1 and the protein contains cystine;

the units A represent from 1 to 70% by weight of the protein derivative; and the units B represent from 0 to 15% by weight of the protein derivative.

The protein from which the protein derivative of the formula (I) is prepared can originate from various sources. Thus, the base protein can originate from a substance of animal origin such as keratin, gelatine, albumin from egg white, blood albumin, casein or lactalbumin. The keratin can originate from hair, wool, horn, fur or bristles and feathers. Likewise, the base protein can originate from a substance of vegetable origin such as soya, groundnut or cotton seeds.

Furthermore, the protein derivative can be a protein hydrolysate which has been chemically modified by hydrolysis for the grafting of the ultraviolet-absorbing radicals.

Preferably, the radical Y of the chemically modified protein derivative of the formula (I) is one of the following radicals:

- a cinnamoyl radical optionally substituted by one or more lower (typically of 1 to 6, especially 1 to 4, carbon atoms) alkoxy groups;
- a para-dialkylaminobenzoyl radical;
- a salicyloyl radical;
- an acyl or sulphonyl radical originating from a carboxylic or sulphonic acid derived from benzylidene-camphor optionally substituted on the aromatic nucleus by one or more alkyl, lower alkoxy or sulpho radicals or by an alkenyl radical carrying one or more alkoxycarbonyl radicals, and/or optionally substituted on the carbon atom in the 10-position of the camphor by a sulpho group;
- a sulphonyl radical originating from an optionally substituted isophthalylidene-camphor or terephthalylidene-camphor radical;
- an acyl or sulphonyl radical originating from a carboxylic or sulphonic acid derived from a heterocyclic absorber which is a 2-arylbenzimidazole, 2-arylbenzofuran, 2-arylbenzoxazole, 2-arylbenzotriazole or 2-arylindole;
- an acyl or sulphonyl radical originating from a carboxylic or sulphonic acid derived from a hydroxybenzophenone absorber;
- an acyl radical derived from an absorber of carboxylic coumarin structure, optionally substituted by one or more lower alkyl or alkoxy radicals;
- an acyl radical derived from an absorber of monophenylcyanoacrylic or diphenylcyanoacrylic structure, optionally substituted on the aromatic nucleus (or nuclei); and
- an acyl or sulphonyl radical derived from an absorber of dibenzoylmethane structure, optionally substituted by one or more hydroxyl or lower alkoxy or alkyl radicals.

The group Y- of the chemically modified protein derivative is particularly one of the following radicals:

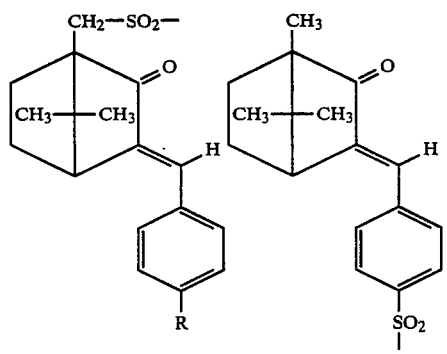

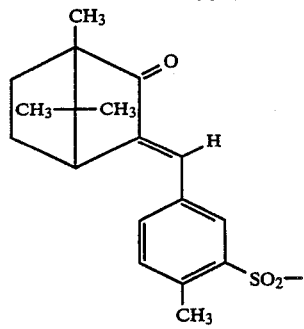

(with R = H, CH₃, Cl or OCH₃)

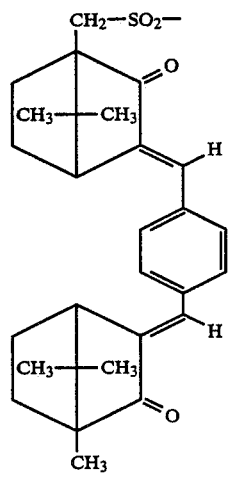

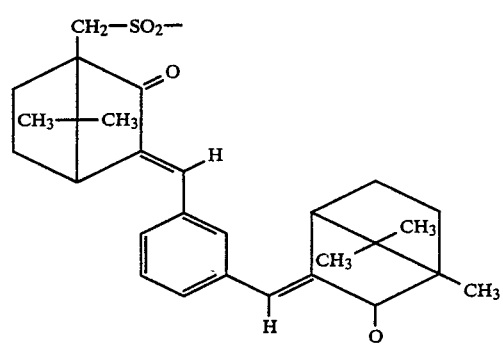

It is also preferred for the chemically modified protein derivative to have a molecular weight of 5,000 to 30,000.

Also, if Z represents $SR_3$, p is preferably equal to 0 and $R_4$ is preferably a hydrogen atom in the formulae (II) and (IV).

The present invention also provides a process for the preparation of the chemically modified protein derivative of the formula (I), characterised in that:

if appropriate, firstly, the starting protein is subjected to acid or enzyme hydrolysis so that the molecular weight of the hydrolysate obtained is about 500 to 50,000;

secondly, radicals absorbing ultraviolet radiation are grafted onto the optionally hydrolysed protein molecule by reacting one or more compounds corresponding to the following formula:

Y-X', in which formula X' represents a halogen atom and Y has the same meaning as above, with all or some of the amino, alcohol, or thiol groups of the optionally hydrolysed protein;

if appropriate, thirdly, and in the case where amine groups are still available after the chemical grafting of the radicals absorbing ultraviolet radiation, an N-alkylation stage is carried out by means of alkylating agent corresponding to one of the following formulae:

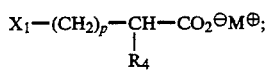  (IIa)

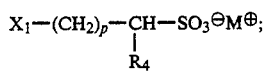  (IIIa)

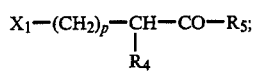  (IVa)

or

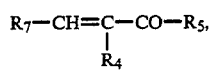  (IV'a)

in which formula $X_1$ represents a halogen atom, $R_4$, $R_5$ and p have the meanings given above and $R_7$ denotes a hydrogen atom or an alkyl radical having at most 4 carbon atoms; and if appropriate, fourthly, and in the case where the protein used conitains cystine units, either: all or some of the disulphidae bridges of the cystine groups of the protein which has undergone the above treatment (or treatments) are oxidised so as to give acid —$SO_3H$ groups, this oxidation optionally being followed by salification of the above-mentioned acid —$SO_3H$ groups, or: all or some of the disulphide bridges of the cystine groups of the protein which has undergone the above treatment (or treatments) are reduced so as to give thiol groups, this reduction being followed by S-alkylation by means of an alkylating agent corresponding to one of the formulae (IIa), (IIIa), ($IV_a$) and ($IV'_a$) defined above.

The process for the preparation of the protein derivative thus comprises successive stages, namely an optional first stage of hydrolysis, a second stage of chemical grafting, an optional third stage of N-alkylation and an optional fourth stage either of oxidation or of S-alkylation on reduced -SH groups. Stages 2, 3 and 4 can be interchanged.

If carried out, the first stage of the process of preparation can be a conventional acid hydrolysis or an enzyme hydrolysis by means of known proteolytic enzymes (e.g. proteinase "PSF 2019", pronase, trypsin, or papain). The operating conditions of hydrolysis vary, according to the enzyme used, as regards the pH and the enzyme/substrate ratio.

The second stage of the process of preparation consists, in particular, of an acylation, the purpose of which is to graft, onto the reactive amino, alcohol or thiol sites of the optionally hydrolysed protein, acyl or sulphonyl radicals originating from one or more molecules absorbing ultraviolet radiation. The acylation is conventionally carried out using a halide, in particular an acid chloride, in an alkaline medium.

If carried out, the third stage of the process of preparation consists of an N-alkylation carried out using an alkylating agent corresponding to one of the formulae (IIa), (IIIa), (IVa) and (IV'a), indicated above. The N-alkylating agent used advantageously corresponds to the following formula: $X_1$—$CH_2CO$—$_2^{\ominus}M^{\oplus}$, $X_1$ and $M^{\oplus}$ having the meanings indicated above. The preferred N-alkylating agent is monochloroacetic acid.

If carried out, the fourth stage of the process can consist either of an oxidation of the disulphide linkages of the cystine groups of the protein, or alternatively of an S-alkylation of the —SH groups obtained by prior reduction of the disulphide bridges of the protein by means of a solution of a reducing agent of conventional type, such as an alkali metal thioglycolate or ammonium thioglycolate.

After the disulphide bridges of the cystine groups of the protein have been broken, oxidation of the protein which has undergone the above treatment (or treatments) makes it possible to convert them to cysteic acid groups. The oxidation is advantageously carried out in an acid medium by means of an oxidising agent such as hydrogen peroxide or a peracid. The oxidation can be followed, if appropriate, by salification of the —$SO_3H$ group.

The S-alkylation is carried out by means of an alkylating agent which corresponds to one of the formulae ($II_a$), ($III_a$), ($IV_a$) and ($IV'_a$), indicated above, the preferred agents and the particularly preferred agent being those indicated for the N-alkylation.

It will, of course, be appreciated that formula (I) is not intended to imply the presence of blocks of units A and, optionally, units B. Rather the formula indicates that units A and, optionally, units B are present along the chain of the protein derivative, the precise location(s) along the chain being unspecified.

The compounds of the invention filter the solar radiation in a wavelength region which depends on the nature of the filter grafted onto the protein derivative.

Thus, if Y- represents a cinnamoyl radical optionally substituted by one or more alkoxy groups, a p-dialkylaminobenzoyl radical, a salicyloyl radical, an acyl radical originating from a carboxylic or sulphonic acid derived from benzylidene-camphor, a sulphonyl radical originating from an isophthalylidene-camphor radical, an acyl radical originating from a carboxylic or sulphonic acid derived from 2-arylbenzimidazoles, 2-arylbenzofurans, 2-arylbenzoxazoles, 2-arylbenzotriazoles, 2-arylindoles or hydroxybenzophenones, or an acyl radical derived from an absorber of carboxylic coumarin structure, the compounds generally absorb in a wavelength region of 280 to 320 nm.

If Y- represents a sulphonyl radical originating from a terephthalylidene-camphor radical, an acyl radical originating from a carboxylic or sulphonic acid derived from 2-arylbenzotriazoles or hydroxybenzophenones, or an acyl radical derived from an absorber of monophenylcyanoacrylic or diphenylcyanoacrylic structure, the compounds generally absorb in a wavelength region of 320 to 380 nm.

If Y- represents an acyl radical derived from an absorber of dibenzoylmethane structure, which is optionally substituted, the compounds generally absorb in a wavelength region of 300 to 380 nm.

The present invention also provides a cosmetic composition which contains, in a suitable carrier, an effective amount of at least one compound of the formula (I), and which can be used as a composition for protecting the human epidermis or as an anti-sunburn composition. The invention also provides a composition which is intended for treating and protecting natural or sensitised hair against any photochemical degradation, and which contains for this purpose, in a suitable carrier, an effective amount of at least one compound of the formula(I). "Sensitised hair" is understood as meaning hair which has undergone a perming, colouring or bleaching treatment.

The compound(s) of the formula (I) is (are) preferably present in the compositions according to the invention in proportion by weight of 0.5 to 15%, relative to the total weight of the composition. Furthermore, they are suitably solubilised in a solvent such as water, a lower monoalcohol or polyol or an aqueous-alcohol solution. The monoalcohols or polyalcohols which are more particularly preferred are ethanol, isopropanol, propylene glycol and glycerol.

The compositions according to the invention can be presented in the diverse forms normally used for this type of composition. In particular, they can be presented in solution in the form of a thickened lotion, in emulsion in the form of a cream or milk or in the form of a gel, or can be packaged in an aerosol can.

The compositions which are intended for protecting or treating the skin can contain the cosmetic adjuvants normally used in this type of composition, such as thickeners, softeners, humectants, superfatting agents, emollients, wetting agents, surface-active agents, preservatives, anti-foam agents, perfumes, oils, waxes, colourants and/or pigments serving to colour the composition itself or the skin, or any other ingredient normally used in cosmetics.

One embodiment of the invention is an emulsion in the form of a protective cream or milk which comprises, in addition to the compound of the formula (I), one or more fatty alcohols, polyoxyethyleneated or polyglycerolated fatty alcohols, fatty acid esters or fatty acid triglycerides, fatty acids, lanoline, natural or synthetic oils or waxes, in the presence of water.

Another embodiment is a lotion such as an oily-alcoholic lotion based on a lower alcohol such as ethanol, or a glycol such as propylene glycol, and/or a polyol such as glycerol, and on a fatty acid ester or fatty acid triglyceride.

There may also be mentioned aqueous-alcoholic lotions based on abovementioned lower alcohols and on water.

The cosmetic composition of the invention can also be an oily-alcoholic gel comprising one or more lower alcohols such as ethanol, propylene glycol or glycerol, and a thickener, in the presence of oil. The alcoholic or aqueous-alcoholic gels comprise one or more abovementioned lower alcohols and a thickener, in the presence of water.

If the compositions according to the invention are used as cosmetic anti-sunburn compositions, they contain at least one compound of the formula (I), which can optionally be associated with another sun filter specific for UV-B radiation or UV-A radiation and compatible therewith. It is thus possible to obtain a formulation which filters out all the UV-B and UV-A rays.

The compositions intended for protecting or treating natural or sensitised hair can be presented in the form of, for example, shampoos, rinse-off lotions, gels or emulsions to be applied before or after shampooing, before or after colouring or bleaching or before or after perming, styling or treatment lotions, blow-drying or setting lotions, hair laquers or compositions for perming, colouring or bleaching the hair. In addition to the compound of the formula (I), these compositions can contain various adjuvants normally used in this type of composition, such as surface-active agents, thickeners, polymers, softeners, preservatives, foam stabilisers, electrolytes, organic solvents, silicone derivatives, oils, waxes, anti-grease agents, colourants and/or pigments serving to colour the composition itself or the hair, and any other ingredient normally used in the field of hair.

If the compositions constitute shampoos, these are essentially characterised in that they contain at least one anionic, non-ionic or amphoteric surface-active agent or a mixture thereof, and a compound of the formula (I), in an aqueous medium. The shampoos can also contain various adjuvants such as cationic surface-active agents, colourants, preservatives, thickeners, foam stabilisers, synergistic agents, softeners, electrolytes, sequestering agents, one or more cosmetic resins, perfumes, natural substances, oils and any other adjuvant used in a shampoo. In these shampoos, the concentration of surface-active agent is generally from 2 to 50% by weight.

Amongst the non-ionic detergents, there may be mentioned, in particular, the condensation products of a monoalcohol, an α-diol, an alkylphenol, an amide or a diglycolamide with glycidol, such as the non-ionic surface-active agents described in French Pat. Nos. 2,091,516, 2,328,763 and 1,477,048, and also polyoxyethyleneated or polyglycerolated fatty alcohols, alkylphenols or acids with fatty chains having from 8 to 18 carbon atoms, and most frequently containing 2 to 30 mol of ethylene oxide, copolymers of ethylene oxide and propylene oxide, condensates of ethylene oxide and propylene oxide with fatty alcohols, polyoxyethyleneated fatty amides, polyoxyethyleneated fatty amines, ethanolamides, fatty acid esters of glycol, fatty acid esters of sorbitol, fatty acid esters of sucrose and glycoside alkyl ethers.

The anionic surface-active agents which can be used, if appropriate mixed with the non-ionic surface-active agents, are chosen, in particular, from the alkali metal salts, the ammonium salts, the amine salts or the aminoalcohol salts of the following compounds:

alkyl-sulphates, oxyethyleneated alkyl-sulphates, alkylamide-sulphates and oxyethyleneated alkylamide-sulphates, polyoxyethyleneated alkylaryl-sulphates and monoglyceride-sulphates, alkylsulphonates, alkylamidesulphonates, alkylarylsulphonates and α-olefinesulphonates, alkyl-sulphosuccinates, oxyethyleneated alkyl-sulphosuccinates and alkylamide-sulphosuccinates, alkyl-sulphosuccinamates, alkyl-sulphoacetates and alkyl-polyglycerolcarboxylates, alkyl-phosphates and oxyethyleneated alkyl-phosphates, alkylsarcosinates, alkylpolypeptidates, alkylamidopolypeptidates, alkylisethionates and alkyltaurates, the alkyl radical in all these compounds containing from 12 to 18 carbon atoms, and fatty acids such as oleic, ricinoleic, palmitic and stearic acids, acids derived from copra oil or from hydrogenated copra oil, and carboxylic acids of polyglycol ethers, corresponding to the formula:

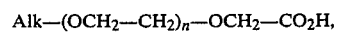

Alk—(OCH$_2$—CH$_2$)$_n$—OCH$_2$—CO$_2$H, in which the substituent Alk corresponds to a linear chain having from 12 to 18 carbon atoms and in which n is an integer from 5 to 15. It is also possible to use any other anionic detergent not mentioned above which is well known in the state of the art.

Amongst the amphoteric surface-active agents which can be used, there may be mentioned, more particularly, alkylamino-monopropionates and alkylamino-dipropionates of betaines such as N-alkylbetaines, N-alkylsulphobetaines and N-alkylamidobetaines, cycloimidinium compounds such as alkylimidazolines, and asparagine derivatives. The alkyl group in these surface-active agents preferably contains at most 22 carbon atoms.

If the compositions constitute leave-on lotions, blow-drying lotions, setting lotions or styling or treatment lotions, they generally comprise, in aqueous, alcoholic or aqueous-alcoholic solution, in addition to the compound of the formula (I), at least one cationic, anionic, non-ionic or amphoteric polymer or a mixture thereof in amounts generally of 0.1 to 10%, and preferably of 0.1 to 3%, by weight, and, if appropriate, one or more anti-foam agents.

If the compositions constitute rinse-off lotions, also called rinses, they are applied before or after bleaching, before or after perming, before or after shampooing or between two stages of shampooing, and are then rinsed off after an interval of time.

These compositions are typically aqueous or aqueous-alcoholic solutions optionally comprising surface-active agents, emulsions or gels. These compositions can also be pressurised in aerosol cans.

The surface-active agents which can be used in the solutions are generally non-ionic or cationic surface-active agents of the type described above for the shampooing compositions, and, in particular, condensation products of a monoalcohol, an α-diol, an alkylphenol, an amide or a diglycolamide with glycidol, such as products of the formula:

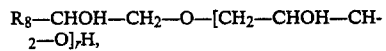

$R_8$—CHOH—CH$_2$—O—[CH$_2$—CHOH—CH$_2$—O]$_r$H, in which $R_8$ denotes an aliphatic, cycloaliphatic or arylaliphatic radical having 7 to 21 carbon atoms, and mixtures thereof, it being possible for the aliphatic chains to contain ether, thioether and hydroxymethylene groups, in which case r denotes a statistical value varying from 1 to 10 inclusive; products of the formula:

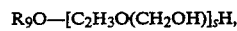

$R_9O$—[C$_2$H$_3$O(CH$_2$OH)]$_s$H, in which $R_9$ denotes an alkyl, alkenyl or alkylaryl radical and s denotes a statistical value varying from 1 to 10 inclusive; and products of the formula:

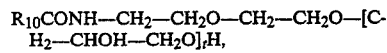

$R_{10}$CONH—CH$_2$—CH$_2$O—CH$_2$—CH$_2$O—[CH$_2$—CHOH—CH$_2$O]$_t$H, in which $R_{10}$ is an aliphatic radical which can optionally contain one or more OH groups and which has from 8 to 30 carbon atoms, and t represents an integer or decimal number from 1 to 5.

It is also possible to use polyoxyethyleneated or polyglycerolated fatty alcohols, alkylphenols or acids with a fatty chain having 8 to 18 carbon atoms, and most frequently containing 2 to 15 mmol of ethylene oxide. The concentration of surface-active agents is suitably from 0.1 to 10%, and preferably from 0.5 to 7% by weight.

Non-ionic, cationic, anionic or amphoteric polymers and, if appropriate, anionic or amphoteric surface-active agents can be added to these compositions.

If the compositions are presented in the form of emulsions, these can be non-ionic or anionic. The non-ionic emulsions consist principally of a mixture of oils and/or fatty alcohols and polyoxyethyleneated fatty alcohols such as polyoxyethyleneated stearyl or cetylstearyl alcohol, in the presence of water. Cationic surface-active agents or cationic polymers can be added to these emulsions.

The anionic emulsions can be made up from soaps and contain the compound (or compounds) of the formula (I) of anionic or non-ionic type.

If the compositions are presented in the form of gels, they contain thickeners, in the presence or absence of solvents. The thickeners which can be used include sodium alginate, gum arabic or cellulose derivatives such as methylcellulose, hydroxymethylcellulose, hydroxyethylcellulose, hydroxypropylcellulose and hydroxypropylmethylcellulose. The lotions can also be thickened by means of a mixture of polyethylene glycol with polyethylene glycol stearate or distearate or by means of a mixture of phosphoric acid esters with amides. The concentration of thickeners is suitably from 0.5 to 30%, and preferably from 0.5 to 15% by weight.

The following Examples further illustrate the present invention.

EXAMPLE 1

Preparation of a hydrolysate of the formula (I), in which formula the proportion of units B is zero, the proportion by weight of units A is about 40%, M+ represents H$^\oplus$ and the unit A has the formula:

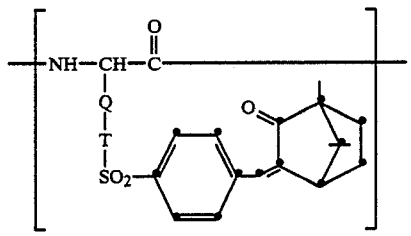

Q representing the alkyl, aryl or aralkyl groups of the aminoacids of keratin and T representing NH or O.

First step: Extraction of keratin from chicken feathers 100 g of washed chicken feathers, 2.1 liters of dimethylformamide and 860 cm$^3$ of water are introduced into a 4 liter reactor. The mixture is heated under reflux for 8 hours and then filtered hot. The filtrate is diluted with 15 liters of water and the precipitate is isolated by filtration. The keratin thus obtained contains between 60 and 80% of water.

The relative analysis of the aminoacids shows similar proportions in the untreated chicken feathers and in the extracted keratin. In both cases, the proportion of cystine is of the order of 7% (between 6.5 and 7.5, depending on the starting material).

Second step: Enzyme hydrolysis of keratin

A keratin obtained as indicated in the first step described above is used as the starting material. A suspension of 5 kg of 30% by weight keratin in 3.5 liters of softened water is prepared; this suspension is heated to 40° C.; the pH is brought to 8.6 by adding a 30% strength by weight aqueous solution of sodium hydroxide.

48 g of proteinase "PSF 2019" are added all at once and the mixture is stirred for 3 hours at 40° C.±1° C., the pH being kept at 8.4–8.6 by adding a 30% strength by weight aqueous solution of sodium hydroxide. The pH of the solution obtained is then adjusted to 7.5 by adding concentrated hydrochloric acid, and the enzyme is deactivated by heating at 95° C. for 5 minutes. The mixture is cooled rapidly to ambient temperature and centrifuged, the supernatant liquid is filtered on cellulose acetate and the solution is lyophilised.

This gives 1,375 g of a water-soluble beige powder. The yield is about 92%.

Third step: Grafting of a molecule with a filtering effect

The following products are introduced into a 2 liter reactor thermostatted at 20° C.±0.2° C.:
- 110 g of hydrolysed keratin obtained in the 2nd step,
- 250 cm³ of water,
- 250 cm³ of acetone and
- 10 cm³ of a 30% strength by weight aqueous solution of sodium hydroxide (the pH is thus brought to 9).

82 g (0.24 mol) of 3-benzylidene-camphor-4'-sulphonyl chloride are then added in small amounts over a period of 1 hour, the pH being kept at between 8.9 and 9.2. The reaction is complete after stirring for 6 hours. The pH of the solution is then brought to 2.5 by adding 30 cm³ of concentrated hydrochloric acid. After dilution in 2 liters of water, a gum is obtained which is separated off by decantation and then taken up in 500 cm³ of water and triturated until crystallisation is complete. The crystals are filtered off, converted to a paste again in 500 cm³ of water, washed twice in succession in 400 cm³ of water, finely ground and dried by lyophilisation after dissolution in water at pH 7.

This gives 95 g of a beige powder. The yield is about 60%.

EXAMPLE 2

Preparation of a hydrolysate of the formula (I) containing 40% by weight of units A and 2.5% by weight of units B, $M^\oplus$ representing $H^\oplus$, the unit A having the same formula as in Example 1 and the unit B containing a group Z of the formula —SCH$_2$COOH.

First step: Reduction of the cystine to cysteine

The product obtained at the end of Example 1 is used as the starting material. The following products are stirred for 20 hours at ambient temperature and under nitrogen:
- 42 g of the product obtained in Example 1,
- 210 cm³ of water,
- 3.1 cm³ of 95% strength by weight thioglycolic acid solution and
- a sufficient amount of sodium hydroxide to bring the pH to 9–9.5.

Second step: S-Carboxymethylation 12.3 g of monochloroacetic acid (0.13 mol) are added to the solution obtained at the end of the first step of this example; the pH is adjusted to 9–9.5 and the mixture is stirred for 2 hours at ambient temperature. It is then acidified to pH 2–2.5 and diluted with water, the precipitate is filtered off, washed with water until the pH of the washings is 6, and dissolved in water at pH 7, and the solution is lyophilised.

This gives a beige powder. The yield is about 88%.

EXAMPLE 3

Preparation of a hydrolysate of the formula (I) containing 39% by weight of units A and 3% by weight of units B, $M^\oplus$ representing $H^\oplus$, A having the same meaning as in Example 1 and B containing a radical Z having the meaning:

$$-S(CH_2)_2-CONH-(CH_2)_3-\overset{\underset{|}{CH_3}}{\overset{|}{\oplus N}}-C_2H_5 \; Br^\ominus.$$
$$\phantom{-S(CH_2)_2-CONH-(CH_2)_3-\oplus N}|$$
$$\phantom{-S(CH_2)_2-CONH-(CH_2)_3-\oplus N}CH_3$$

The solution obtained at the end of the first step of Example 2 is used as the starting material. 34.5 g (0.13 mol) of 1-dimethylethylammonio-3-acrylamidopropane bromide are added to this amount of solution and the mixture is stirred for 4 hours at ambient temperature and at pH 9–9.5.

After acidification with a dilute hydrochloric acid solution, the solid is filtered off, washed several times in succession and dissolved at pH 7 and the solution is lyophilised. This gives 31 g of a beige powder. The yield is about 74%.

EXAMPLE 4

Preparation of a hydrolysate at the formula (I) containing 30% by weight of units A corresponding to the formula:

in which Q represents the alkyl, aryl or aralkyl groups of the aminoacids of keratin and T represents NH or O, $M^\oplus$ having the meaning $H^\oplus$ and the proportion of units B being zero.

The hydrolysate obtained at the end of the second step of Example 1 is used as the starting material. The following products are introduced into a 2 liter reactor thermostatted at 20° C.±0.2° C.:
- 70 g of hydrolysed keratin obtained at the end of the second step of Example 1,
- 175 cm³ of water,
- 175 cm³ of acetone,
- 5 cm³ of a 30% strength by weight aqueous solution of sodium hydroxide and
- 54 g of 3-benzylidene-camphor-b 10-sulphonyl chloride (0.16 mol).

After stirring for 2 hours, a precipitate of sodium 3-benzylidene-camphor-10-sulphonate appears, which is removed by filtration.

The filtrate is treated as in the third step of Example 1. This gives 36 g of a beige powder. The yield is about 34%.

EXAMPLE 5

Preparation of a hydrolysate of the formula (I) containing 33% by weight of units A having the same formula as in Example 4, and 3.5% by weight of units B, the group Z which appears in the units B having the meaning —SCH$_2$COOH and M$^\oplus$ representing H$^\oplus$.

The following mixture is prepared:
- 23 g of the product obtained at the end of Example 4,
- 200 cm$^3$ of water,
- 2.95 cm$^3$ of 95% strength by weight thioglycolic acid solution and
- a sufficient amount of a 30% strength by weight aqueous solution of sodium hydroxide to bring the pH to 9–9.5.

The mixture is stirred for 20 hours at ambient temperature and under nitrogen. 11.34 g (0.12 mol) of monochloroacetic acid are then added and the pH is adjusted to 9–9.5 with a 30% strength by weight aqueous solution of sodium hydroxide. After stirring for 4 hours, a small amount of insoluble material is filtered off, the filtrate is acidified to pH 2–2.5 and diluted with water, the precipitate is filtered off, washed with water until the pH of the washings is 6, and dissolved in water at pH 7, and the solution is then lyophilised. This gives 20 g of a beige powder. The yield is about 87%.

EXAMPLE 6

Preparation of a hydrolysate of the formula (I) containing 14.5% of units A corresponding to the formula:

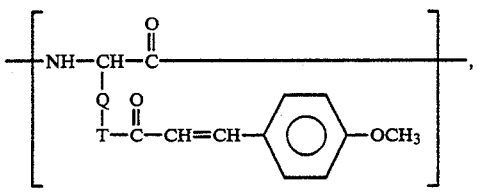

in which formula Q represents the alkyl, aryl or aralkyl groups of the aminoacids of keratin and T represents NH or O, the proportion of units B being zero and M$^\oplus$ representing H$^\oplus$.

The following products are introduced into a 2 liter reactor thermostatted at 10±0.2° C.:
- 53 g of the product obtained at the end of the second step of Example 1,
- 125 cm$^3$ of water,
- 125 cm$^3$ of acetone and
- a sufficient amount of a 30% strength by weight aqueous solution of sodium hydroxide to bring the pH to 9.

29 g (0.147 mol) of p-methoxycinnamoyl chloride are then added over a period of 1 hour; for 2 hours, on the one hand the stirring and the temperature are maintained, and on the other hand the pH is kept at a value of between 8.5 and 9.

The mixture is then allowed to return to ambient temperature over a period of 2 hours; it is acidifed to pH 6 with a 6N hydrochloric acid solution, the precipitate of p-methoxycinnamic acid formed is filtered off and washed twice with 200 cm$^3$ of water, and the filtrate is acidified to pH 5.5. The latter is then extracted with three times 300 cm$^3$ of ether and subsequently precipitated by acidification to pH 2.5 with concentrated hydrochloric acid and then by dilution in 500 cm$^3$ of water.

This gives a gum, which is separated off by decantation and taken up in water; the precipitate obtained is filtered off and washed with water until the pH of the washings is 6. After grinding, dissolution in water at pH 7 and lyophilisation, 25 g of a beige powder are obtained. The yield is 33%.

EXAMPLE 7

Preparation of a hydrolysate of the formula (I) containing 30% of units A, the units A having the formula:

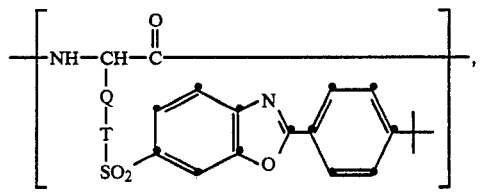

in which formula Q represents the alkyl, aryl or aralkyl groups of the aminoacids of keratin and T represents NH or O, the proportion of units B being zero and M$^\oplus$ representing H$^\oplus$.

The following products are introduced into a 2 liter reactor thermostatted at 20° C.±0.2° C.:
- 50 g of hydrolysed keratin obtained at the end of the second step of Example 1,
- 250 cm$^3$ of water,
- 250 cm$^3$ of acetone and
- a sufficient amount of a 30% strength by weight aqueous solution of sodium hydroxide to bring the pH to 9.

45 g (0.128 mol) of 2-p-tert.-butylphenylbenzoxazole-6-sulphonyl chloride are added over a period of 4 hours and the mixture is stirred for 48 hours at 20° C., the pH being kept at 8.5–9. A small amount of insoluble material is filtered off, the filtrate is acidified to pH 5.5 with a dilute hydrochloric acid solution, extracted with three times 250 cm$^3$ of ether, acidified to pH 2 with 0.5N hydrochloric acid and diluted with 1 liter of water, and the gum obtained is separated off by decantation.

The gum is then taken up in water; the precipitate obtained is filtered off and washed with water until the pH of the washings is 6. After grinding, dissolution in water at pH 7 and lyophilisation, 13 g of a beige powder are obtained. The yield is about 15%.

EXAMPLE 8

Preparation of a protein derivative of the formula (I), in which formula the proportion of units B is zero, the proportion by weight of units A is about 20%, M$^+$ represents H$^\oplus$ and the unit A has the formula:

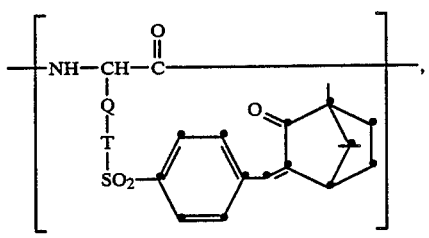

Q representing the alkyl, aryl or aralkyl groups of the aminoacids of gelatin and Y representing NH or O.

The following products are introduced into a reactor thermostatted at 35° C:
250 cm³ of water,
100 g of ASF ROUSSELOT gelatin (content of amino nitrogen: 1.75 meq/g) and
250 cm³ of acetone.

The pH is brought to 9 by adding 30% strength by weight sodium hydroxide solution.

59 g (0.174 mol) of 3-benzylidene-camphor-4'-sulphonyl chloride are then added over a period of 3 hours, the pH of the reaction mixture being kept at between 8.9 and 9.2 by adding 30% strength by weight sodium hydroxide solution. After a reaction time of 5 hours at 35+ C., the pH of the solution is then brought to 2.5 by adding 16 cm³ of concentrated hydrochloric acid. The precipitate formed is filtered off, washed with water until the pH of the washings is 4, and then redissolved in 75 cm³ of a 5% strength aqueous solution of sodium hydroxide. After lyophilisation, 106 g of a beige powder are obtained. The yield is about 70%.

EXAMPLE 9

Preparation of a protein derivative of the formula (I), in which formula the proportion of units B is zero, the proportion by weight of units A is about 25%, $M^\oplus$ represents $H^\oplus$ and the unit A has the formula:

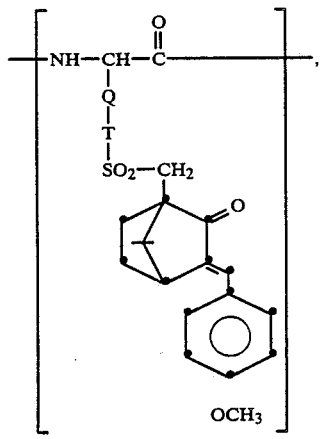

Q representing the alkyl, aryl or aralkyl groups of the aminoacids of casein and T representing NH or O.

First step: Enzyme hydrolysis of the casein 100 g of edible casein are suspended in 1 liter of water. The pH is adjusted to between 1.8 and 2.0 by adding 35% strength hydrochloric acid. After the temperature has stabilised at 38±1° C., 0.2 g of 1:60,000 SIGMA ® pepsin is added. Stirring is maintained for 8 hours at this temperature, the enzyme is then deactivated at pH 8–8.5 for 10 hours and the solution is ultrafiltered so as to remove the inorganic salts and the molecular weight fraction below 1,000. After lyophilisation, 85 g of a hydrolysate are obtained which has an amine content of 2.54 meq/g.

Second step: Grafting of a molecule with a filtering effect.

A hydrolysed casein obtained as indicated in the first step is used as the starting material. The same procedure as that described in Example 8 is followed, except that the gelatin is replaced by hydrolysed casein (content of amino nitrogen: 2.54 meq/g) and that the derivative absorbing ultraviolet radiation is 4'-methoxy-3-benzylidene-camphor-10-sulphonyl chloride.

The yield is 52%.

EXAMPLE 10

Preparation of a protein derivative of the formula (I), in which formula the proportion of units B is zero, the proportion by weight of units A is about 25%, $M^\oplus$ represents $H^\oplus$ and the unit A has the formula:

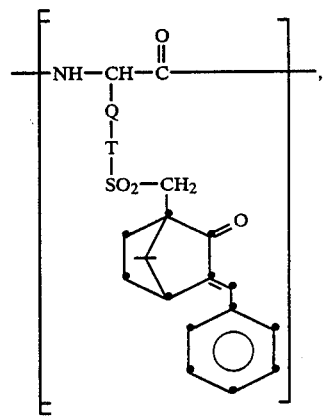

Q representing the alkyl, aryl or aralkyl groups of the aminoacids of casein and T representing NH or O.

The product obtained at the end of the first step of Example 9 is used as the starting material. The same procedure as that described in Example 8 is then followed, except that the gelatin is replaced by hydrolysed casein (content of amino nitrogen: 2.54 meq/g) and that the derivative absorbing ultraviolet radiation is 3-benzylidene-camphor-10-sulphonyl chloride.

The yield is 43%.

EXAMPLE 11

Preparation of a protein derivative of the formula (I), in which formula the proportion of units B is zero, the proportion by weight of units A is about 20%, $M^\oplus$ represents $H^\oplus$ and the unit A has the formula:

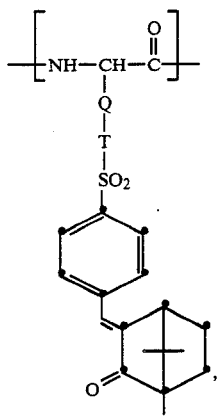

Q representing the alkyl, aryl or aralkyl groups of the aminoacids of casein and T representing NH or O.

The product obtained at the end of the first step of Example 9 is used as the starting material. The same procedure as that described in Example 8 is then followed, except that the gelatin is replaced by hydrolysed casein (content of amino nitrogen: 2.54 meq/g) and that the derivative absorbing ultraviolet radiation is 3-benzylidene-camphor-4'-sulphonyl chloride.

The yield is 50%.

EXAMPLE 12

Preparation of a protein derivative of the formula (I), in which formula the proportion of units B is zero, the proportion by weight of units A is about 60%, $M^{\oplus}$ represents $H^{\oplus}$ and the unit A has the formula:

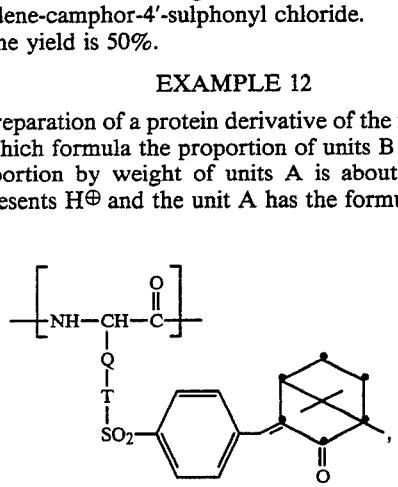

Q representing the alkyl, aryl or aralkyl groups of the aminoacids of lactalbumin and T representing NH or O.

The procedure described in Example 8 is followed, except that the gelatin is replaced by hydrolysed lactalbumin (content of amino nitrogen: 5.6 meq/g).

The yield is 58%.

Table 1 gives a number of properties of the protein derivatives obtained in Examples 1 to 12.

TABLE 1

| Example | Solubility in H₂O at pH 7 (by weight) | UV H₂O λmax (nm) | E(1%)* | % of filter fixed | % of filter fixed, determined by hydrolysis | % of protein material | Free aminoacids |
|---|---|---|---|---|---|---|---|
| 1 | ≧20% | 300 | 225 | 30% | 40% | 41% | NO |
| 2 | ≧20% | 297 | 302 | 40% | 40% | 43% | NO |
| 3 | ≧20% | 300 | 308 | 41% | 39% | 38.5% | NO |
| 4 | ≧20% | 300 | 207 | 31% | 30% | 48.5% | 0.4% |
| 5 | ≧20% | 297 | 286 | 41% | 33% | 58.3% | NO |
| 6 | ≧20% | 310 | 215 | 15% | 14.5% | 76% | NO |
| 7 | ≧20% | 302 | 375 | 27% | 30% | 40.4% | NO |
| 8 | ≧20% | 298 | 228 | 31% | 25% | 75% | NO |
| 9 | ≧20% | 322 | 154 | 23% | 18% | 65% | NO |
| 10 | ≧20% | 297 | 183 | 25% | 20% | 65% | NO |
| 11 | ≧20% | 295 | 240 | 33% | 20% | 60% | NO |
| 12 | ≧20% | 297 | 743 | 60% | 40% | 60% | NO |

*E(1%) represents the optical density, measured at the wavelength of the absorption maximum, for an aqueous solution containing 1% by weight of filtering product.

EXAMPLE 13

A protective day cream having the following formulation is prepared:
Compound of Example 1—2 g
Stearic acid—3 g
Self-emulsifiable glycerol stearate—3 g
Cetyl alcohol—2 g
Vaseline oil—10 g
Grapeseed oil—3 g
Sunflower oil—2 g
Triethanolamine—1 g
Methyl para-hydroxybenzoate—0.2 g
Perfume—0.3 g
Antioxidants—q.s.
Demineralised water q.s.—100 g It is found that repeated use of this composition gives the skin a good protection against the weather, while at the same time leaving it soft and supple.

EXAMPLE 14

A protective moisturising cream having the following formulation is prepared:
Compound of Example 3—3 g
Zinc lanolate—2.7 g
Lanoline alcohol—3 g
Vaseline oil—22 g
Vaseline—15 g
Methyl para-hydroxybenzoate—0.3 g
Perfume—q.s.
Demineralised water q.s.—100 g It is found that repeated use of this cream gives the skin suppleness and softness, whilst at the same time preventing it from drying out.

EXAMPLE 15

A protective handcream having the following formulation is prepared:
Compound of Example 5—2 g
Polyethylene glycol stearate (containing 20 mol of ethylene oxide) sold under the name "MYRJ 49" by "ATLAS"—3 g
Self-emulsifiable glycerol stearate—3 g
Cetyl alcohol—1 g Vaseline oil—15 g
High molecular weight carboxyvinylic polymer derived from acrylic acid, sold under the name "CARBOPOL 940" by "GOODRICH CHEMICAL"—0.3 g
Triethanolamine—0.3 g
Preservatives—q.s.
Perfume—q.s.
Demineralised water q.s.—100 g It is found that repeated use of this handcream protects the hands from daily attack and gives them softness.

EXAMPLE 16

A sun cream having the following formulation is prepared:
Compound of Example 2—5 g
Cetyl-stearyl alcohol and oleyl-cetyl alcohol both oxyethyleneated with 25 mol of ethylene oxide—7 g
Glycerol monostearate—2 g
Vaseline oil—15 g
Dimethylpolysiloxane—1.5 g
Cetyl alcohol—1.5 g
Glycerol—20 g
Preservatives, perfume—q.s.
Sterile demineralised water q.s.—100 g It is found that repeated use of this cream leaves the skin soft and supple, whilst at the same time providing a good protection against the sun.

EXAMPLE 17

A sun milk having the following formulation is prepared:
Compound of Example 7—4 g
Cetyl-stearyl alcohol and oleyl-cetyl alcohol both oxyethyleneated with 25 mol of ethylene oxide—5 g
Vaseline oil—6 g
Isopropyl myristate—3 g
Silicone oil—1 g
Cetyl alcohol—1 g
Preservatives, perfumes—q.s.
Sterile demineralised water q.s.—100 g It is found that repeated use of this milk leaves the skin soft and supple, whilst at the same time providing a good protection against the sun.

EXAMPLE 18

A shampoo having the following formulation is prepared:
Compound of Example 1—1.2 g
Triethanolamine alkyl($C_{12}$-$C_{14}$)-sulphate—8.0 g
Cycloimidazoline derivative of coconut oil, sold under the name "MIRANOL C2M" by "MIRANOL"—4.0 g
pH adjusted to 7.5 with HCl
Water q.s.—100 g When applied to natural hair, this shampoo gives the hair softness and shine.

When applied to dyed hair, it protects it from the external atmospheric agents.

EXAMPLE 19

A shampoo having the following formulation is prepared:
Compound of Example 3—1.5 g
Non-ionic surface-active agent of the formula: R—CHOH—$CH_2$—O—($CH_2$—CHOH—$CH_2$—O)$_n$H, in which R represents a mixture of $C_9$-$C_{12}$ alkyl radicals and n represents an average statistical value of 3.5—8 g
Lauric diethanolamide—1.5 g
NaCl—3.5 g
pH adjusted to 7.3
Water q.s.—100 g When applied to dyed hair, this shampoo gives softness and ease of comb-out and protects it from the external atmospheric agents.

EXAMPLE 20

An after-shampoo (rinse) having the following formulation is prepared:
Compound of Example 5—1 g
Mixture of cetyl-stearyl alcohol and cetyl-stearyl alcohol oxyethyleneated with 1.5 mol of ethylene oxide, sold under the name "SINNOWAX AO" by "HENKEL"—3 g
Mixture of fatty alcohols and oxyethyleneated products, sold under the name "POLAWAX GP 200∞ by "CRODA"—1.5 g
Hydroxyethylcellulose sold under the name "CELLOSIZE QP 4400" by "UNION CARBIDE"—0.5 g
pH adjusted to 7
Demineralised water q.s.—100 g This composition is applied to clean and damp hair for 5 to 10 minutes; the hair is then rinsed and dried. The hair is shiny.

EXAMPLE 21

A setting lotion having the following formulation is prepared:
Compound of Example 4—0.8 g
60/40 Vinylpyrrolidone/vinyl acetate copolymer—0.5 g
Trimethylcetylammonium bromide—0.2 g
Water q.s.—100 g This lotion is applied to clean hair. The dried hair is easy to comb out and is protected from the external atmospheric agents.

EXAMPLE 22

A water-resistant cream having the following formulation is prepared:
Compound of Example 8—2 g
2-Ethylhexyl p-dimethylaminobenzoate—4 g
Lauric acid ester of sorbitol, containing 20 mol of ethylene oxide—4.5 g
Polyphenylmethylsiloxane sold under the name "Silicone DC 556"—5 g
Glyceryl monostearate—4.5 g
Sorbitan monolaurate—4 g
Stearic acid—5 g
Glycerol—3.5 g
Magnesium aluminium silicate—2 g
Perfume
Preservative: mixture of 5-chloro-2-methyl-4-isothiazolin-3-one, 2-methyl-4-isothiazolin-3-one and magnesium and calcium chlorides in 1.5% strength aqueous solution, sold under the name "KATHON CG" by "ROHM and HAAS"—0.2 g
Water q.s.—100 g This sun cream protects the skin from the UV-B radiation, whilst leaving it soft and supple.

EXAMPLE 23

A sun cream having the following formulation is prepared:
Compound of Example 11—4 g
Stearic acid—5 g
Sorbitol—3 g
Lanoline—2 g
Isopropyl myristate—2 g
Cetyl alcohol—0.15 g
Propyl para-hydroxybenzoate—0.1 g
Acrylic acid polymer having a molecular weight of 2 to 3 million, sold under the name "CARBOPOL 934" by "GOODRICH CHEMICAL CO"—0.1 g
Perfume
Triethanolamine q.s. pH 7
Water q.s.—100 g
The same results are observed as in Example 22.

EXAMPLE 24

A sun cream having the following formulation is prepared:
Compound of Example 10—5 g
Mineral oil—21 g
Self-emulsifiable glyceryl monostearate—7 g
Spermaceti wax—1.5 g
Stearic acid—2 g
Glycerol—2.5 g
Lanoline alcohol containing 5 mol of ethylene oxide—1 g
Methyl para-hydroxybenzoate—0.1 g
Propyl para-hydroxybenzoate—0.1 g
Perfume
Water q.s.—100 g
The same results are observed as in Example 22.

EXAMPLE 25

A sun cream consisting of an oil-in-water emulsion and having the following formulation is prepared:
Compound of Example 8—2 g
4-(2-Oxobornylidene-3-methyl)-phenyltrimethyl-ammonium methyl-sulphate (UV-B filter)—4 g
Isopropyl myristate—4.3 g
Triethanolamine lauryl-sulphate—0.8 g
Diethylene glycol monostearate—2 g
Cetyl alcohol—0.5 g
Stearic acid—3.5 g
Perfume
Methyl para-hydroxybenzoate—0.15 g
Triethanolamine—1 g
Water q.s.—100 g
The same results are observed as in Example 22.

EXAMPLE 26

A sun gel having the following formulation is prepared:
Compound of Example 11—8 g
Sodium salt of 2-phenylbenzimidazole-5-sulphonic acid—3 g
Acrylic acid polymer having a molecular weight of 2 to 3 million, sold under the name "CARBOPOL 934" by "GOODRICH CHEMICAL CO"—0.1 g
Hexane-1,2,6-triol—14 g
Sodium hydroxide—0.4 g
Perfume
Water q.s.—100 g It is found that repeated use of this gel leaves the skin soft and supple, whilst at the same time giving a good protection against the sun.

EXAMPLE 27

A sun lotion having the following formulation is prepared:
Compound of Example 12—3 g
Mineral oil—25 g
Sorbitan monostearate—1.5 g
Sorbitan monostearate containing 20 mol of ethylene oxide—9 g
Propyl para-hydroxybenzoate—0.1 g
Water q.s.—100 g
This lotion gives a good protection against the sun and prevents the skin from drying out.

EXAMPLE 28

A sun aerosol having the following formulation is prepared:
Compound of Example 10—1 g
Ethyl alcohol—33 g
Glycerol—3 g
Castor oil—21 g
Stearyl alcohol containing 2 mol of ethylene oxide—5 g
Water—29 g
Propellant: dichlorodifluoromethane (Freon 12)/dichlorotetrafluoroethane (Freon 114) in a ratio of 40/60—8 g
The same results are observed as in the previous example.

EXAMPLE 29

A protective day cream having the following formulation is prepared:
Compound of Example 11—2 g
Self-emulsifiable glycerol stearate—5 g
Cetyl alcohol—1 g
Stearic acid—5 g
Vaseline oil—10 g
Glycerol—3 g
Methyl para-hydroxybenzoate—0.3 g
High molecular weight carboxyvinylic polymer sold under the name "CARBOPOL 940" by GOODRICH CHEMICAL CO—0.4 g
Triethanolamine—0.4 g
Water q.s.—100 g
Repeated use of this composition gives the skin a good protection against the weather, whilst leaving it soft and supple.

EXAMPLE 30

A protective moisturising emulsion for the body, having the following formulation, is prepared:
Compound of Example 9—2 g
Polyethylene glycol stearate sold under the name "MYRJ 49" by "ATLAS"—0.8 g
Self-emulsifiable glycerol stearate—2 g
Cetyl alcohol—0.5 g
Sesame oil—10 g
Stearic acid—2 g
Glycerol—3 g
Methyl para-hydroxybenzoate—0.3 g
Acrylic acid polymer having a molecular weight of 2 to 3 million, sold under the name "CARBOPOL 934" by "GOODRICH CHEMICAL CO"—0.2 g
Triethanolamine—0.2 g Perfume—0.8 g
Water q.s.—100 g Repeated use of this emulsion leaves the skin soft and supple.

EXAMPLE 31

A protective moisturising cream having the following formulation is prepared:
Compound of Example 8—3 g
Magnesium lanolate—3.25 g
Lanoline alcohol—7.50 g
Vaseline oil—22 g
Perhydrosqualene—15 g
Vaseline—12.25 g
Methyl para-hydroxybenzoate—0.3 g
Demineralised water q.s.—100 g The same results are observed as in Example 29.

EXAMPLE 32

A shampoo having the following formulation is prepared:
Compound of Example 8—0.3 g
Sodium salt of sulphated alkanol($C_{12}$–$C_{14}$) oxyethyleneated with 2.2 mol of ethylene oxide 8.0 g
Lauric diethanolamide—1.5 g
NaCl—3.5 g
pH adjusted to 7.3 with HCl
Water q.s.—100 g When applied to natural hair, this shampoo leaves it soft and shiny; when applied to dyed hair, it protects it from the external atmospheric agents.

EXAMPLE 33

A shampoo having the following formulation is prepared:
Compound of Example 11—1.0 g
R-CHOH-$CH_2$O-($CH_2$-CHOH-$CH_2$O)$_n$H in which R represents a mixture of $C_9$–$C_{12}$ alkyl radicals and n has an average statistical value of about 3.5—10.0 g
Hydroxyethylcellulose, sold under the name "NATROSOL 250 HHR" by "HERCULES"—0.6 g
pH adjusted to 7 with NaOH
Water q.s.—100 g The same results are observed as in the previous example.

EXAMPLE 34

A rinse having the following formulation is prepared:
Compound of Example 8—0.8 g
Mixture of cetyl-stearyl alcohol and cetyl-stearyl alcohol oxyethyleneated with 1.5 mol of ethylene oxide, sold under the name "SINNOWAX AO" by "HENKEL"—3.0 g
Mixture of fatty alcohols and oxyethyleneated products, sold under the name "POLAWAX GP 200" by "CRODA"—1.5 g
Hydroxyethylcellulose sold under the name "CELLOSIZE QP 4400" by "UNION CARBIDE"—0.5 g
pH adjusted to 5 with HCl
Water q.s—100 g This composition is applied to clean and damp hair for about ten minutes; the hair is then rinsed. The hair is soft, and repeated use of this composition gives it a good protection from the atmospheric agents.

EXAMPLE 35

A rinse-off after-shampoo in the form of an aerosol foam, the active principle of which has the following formulation, is prepared:
Compound of Example 11—2.0 g
Lauryl alcohol polyoxyethyleneated with 12 mol of ethylene oxide—0.5 g
Water q.s—100 g
pH adjusted to 7.2 with HCl Packaging as an aerosol was carried out with a propellant consisting of a mixture of dichlorodifluoromethane (Freon 12) and dichlorotetrafluoroethane (Freon 114) in a ratio of 50/50, in proportions of 90% by weight of active principle and 10% by weight of propellant.

The same results are observed as in the previous example.

We claim:

1. A chemically modified protein derivative which has a molecular weight of about 500 to 50,000 and which corresponds to the following general formula:

$$NH-P_1-\left[-NH-CH-\underset{Q}{\underset{|}{C}}-\right]-\left[-NH-CH-\underset{(CH_2)_q}{\underset{|}{C}}-\right]-P_2-CO_2^{\ominus}M^{\oplus} \quad (I)$$

$$\underset{A}{\phantom{X}} \qquad \underset{B}{\phantom{X}}$$

(with Y on $P_1$, T—Y on Q in block A, and Z on $(CH_2)_q$ in block B)

in which formula:
Y is a radical of a molecule—capable of absorbing ultraviolet radiation;
$P_1$ and $P_2$ are independently chain protein units which are not acylated or chemically modified by nucleophilic addition or substitution; $N^+(R_2)_4$, in $M^+$ represents $H^+$, a cation derived from an alkali metal or from half an atom of magnesium, or $N^+(R_2)_4$, in which formula the radicals $R_2$ are identical or different and represent a hydrogen atom or an alkyl or hydroxyalkyl radical having at most 4 carbon atoms;
each Q is independently an alkyl, aryl or aralkyl radical of a constituent aminoacid of the protein;
T represents O, NH or, if the protein contains one or more cysteine units, S;
Z is:
(i) a radical $SO_3$—$M^+$, the cation $M^+$ being as defined; or
(ii) $SR_3$, in which formula $R_3$ represents:

$$-(CH_2)_p-\underset{R_4}{\underset{|}{CH}}-CO_2^{\ominus}M^{\oplus}; \quad (II)$$

$$-(CH_2)_p-\underset{R_4}{\underset{|}{CH}}-SO_3^{\ominus}M^{\oplus}; \text{ or} \quad (III)$$

$$-(CH_2)_p-\underset{R_4}{\underset{|}{CH}}-CO-R_5; \quad (IV)$$

in which formulae p is 0 or an integer from 1 to 5, $R_4$ is a hydrogen atom or an alkyl radical having at most 4 carbon atoms and $R_5$ represents:

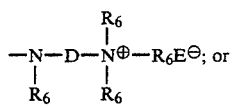

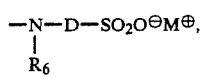

in which formulae D is a linear or branched alkylene group containing a total of from 2 to 10 carbon atoms, the cation $M^{\oplus}$ is as defined above, the radicals $R_6$ being identical or different and representing a hydrogen atom or an alkyl or hydroxyalkyl radical having at most 4 carbon atoms, and $E^{\ominus}$ being a halide ion or $RCOO^{\ominus}$, $RSO_3^{\ominus}$ or $RSO_4^{\ominus}$, R representing a hydrocarbon rest containing from 1 to 10 carbon atoms; or alternatively (iii) an amino radical originating from a basic aminoacid of the protein, monosubstituted or disubstituted by a radical $R_3$;

q is an integer from 1 to 5, with the proviso that, if Z represents a radical $SO_3^{\ominus}M^{\oplus}$ or $SR_3$, q is necessarily equal to 1 and the protein contains cystine units; the units A represent from 1 to 70% by weight of the protein derivative; and the units B represent from 0 to 15% by weight of the protein derivative.

2. A protein derivative according to claim 1, in which the protein from which it is obtained is a protein originating from keratin, gelatin, egg white albumin, blood albumin, casein or lactalbumin.

3. A protein derivative according to claim 1, in which the protein from which it is obtained is a protein originating from soya, groundnut or cotton seeds.

4. A protein derivative according to claim 1, which is derived from a protein hydrolysate which is chemically modified after the hydrolysis by which it has been produced.

5. A protein derivative according to claim 1, in which the radical Y is one of the following radicals:
a cinnamoyl radical optionally substituted by one or more lower alkoxy groups;
a para-dialkylaminobenzoyl radical;
a salicyloyl radical;
an acyl or sulphonyl radical of a carboxylic or sulphonic acid derived from benzylidene-camphor optionally substituted on the aromatic nucleus by one or more alkyl, lower alkoxy or sulpho radicals or by an alkenyl radical carrying one or more alkoxycarbonyl radicals, and/or optionally substituted on the carbon atom in the 10-position of the camphor by a sulpho group;
a sulphonyl radical of an optionally substituted isophthalylidene-camphor or terephthalylidene-camphor radical;
an acyl or sulphonyl radical of a carboxylic or sulphonic acid derived from a heterocyclic absorber which is a 2-arylbenzimidazole, 2-arylbenzofuran, 2-arylbenzoxazole, 2-arylbenzotriazole or 2-arylindole;
an acyl or sulphonyl radical of a carboxylic or sulphonic acid derived from a hydroxybenzophenone absorber;
an acyl radical of a carboxylic coumarin absorber, optionally substituted by one or more lower alkyl or alkoxy radicals;
an acyl radical of a monophenylcyanoacrylic or diphenylcyanoacrylic absorber, optionally substituted on the aromatic nucleus (or nuclei); or
an acyl or sulphonyl radical of a dibenzoylmethane absorber, optionally substituted by one or more hydroxyl or lower alkoxy or alkyl radicals.

6. A protein derivative according to claim 5, in which the group Y— is one of the following radicals:

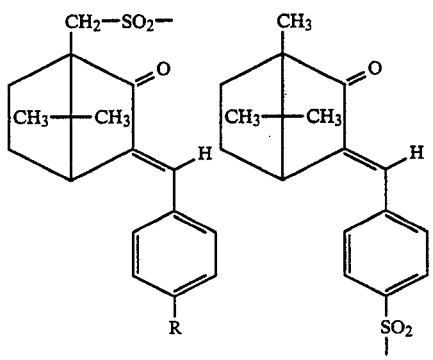

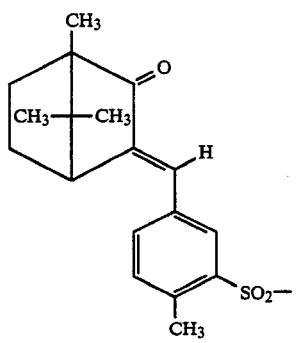

(with R = H, $CH_3$, Cl or $OCH_3$)

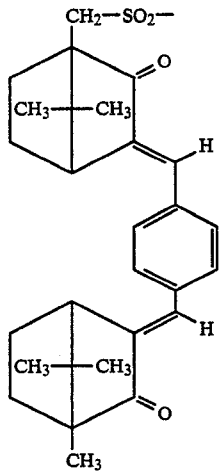

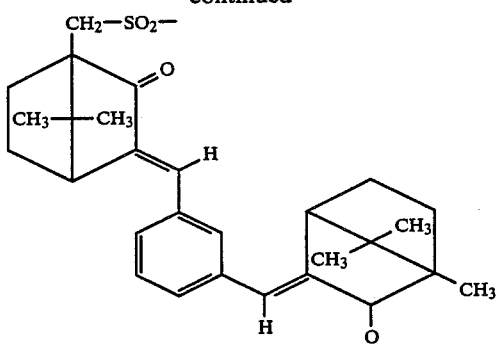

7. A protein derivative according to claim 1 which has a molecular weight of 5,000 to 30,000.

8. A protein derivative according to claim 1 in which Z represents $SR_3$ in which $R_3$ corresponds to the formula (II) or (IV), $R_4$ is a hydrogen atom and p is equal to 0.

9. Process for the preparation of the protein derivative as defined in claim 1 which comprises:

firstly, optionally subjecting a protein to acid or enzyme hydrolysis so that the molecular weight of the hydrolysate obtained is from about 500 to 50,000;

secondly, grafting one or more radicals absorbing ultraviolet radiation onto the optionally hydrolysed protein by reacting it with one or more compounds corresponding to the following formula:

Y-X', in which formula X' represents a halogen atom and Y is as defined in claim 1;

optionally, if any amino groups remain after the grafting, reacting the product with an alkylating agent corresponding to one of the following formulae:

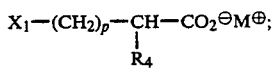 (IIa)

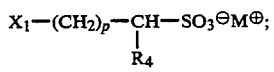 (IIIa)

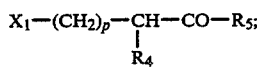 (IVa)

or

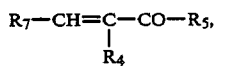 (IV'a)

in which formula $X_1$ represents a halogen atom, $R_4$, $R_5$ and p are as defined in claim 1 and $R_7$ denotes a hydrogen atom or an alkyl radical having at most 4 carbon atoms; and optionally, when the protein contains cystine, oxidising all or some of the disulphide bridges of the cystine groups of the treated protein so as to give acid —$SO_3H$ groups, this oxidation optionally being followed by salification of the abovementioned acid —$SO_3H$ groups, or reducing all or some of the disulphide bridges of the cystine groups of the treated protein to give thiol groups —SH, this reduction being followed by S-alkylation with an alkylating agent corresponding to one of the formulae (IIa), (IIIa), (IVa) and (IV'a) as defined above.

10. Process according to claim 9, in which the S-alkylating or N-alkylating agent used corresponds to the formula:

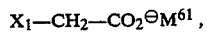

in which formula $X_1$ and $M^\oplus$ are as defined in claim 9.

11. Process according to claim 9, in which the oxidation is carried out in an acid medium with hydrogen peroxide or a peracid.

12. A cosmetic composition suitable for treating the skin which comprises, in the presence of a cosmetically acceptable carrier, an effective amount of at least one protein derivative as claimed in claim 1.

13. A composition suitable for treating natural or sensitised hair which comprises, in the presence of a suitable carrier, an effective amount of at least one protein derivative as claimed in claim 1.

14. A composition according to claim 12 in which the protein derivative is present in an amount by weight of 0.5 to 15%, relative to the total weight of the composition.

15. A composition according to claim 13 in which the protein derivative is present in an amount by weight of 0.5 to 15%, relative to the total weight of the composition.

16. A composition according to claim 12, in which the protein derivative is solubilised in water, a lower mono-alcohol or polyol or an aqueous-alcoholic solution.

17. A composition according to claim 12, which contains at least one thickener, softener, humectant, superfatting agent, emollient, wetting agent, surface-active agent, preservative, anti-foam agent, oil, wax, colourant or pigment.

18. A composition according to claim 12, which is a solution in the form of a lotion, an emulsion in the form of a cream or milk or a gel, or is packaged in an aerosol can.

19. A composition according to claim 13, which contains at least one non-ionic, anionic, cationic or amphoteric surface-active agent, an animal, mineral, vegetable or synthetic oil or wax, a silicone derivative, fatty alcohol, anionic, cationic, non-ionic or amphoteric resin, emulsifying agent, sun filter compatible with a derivative of formula (I), an organic solvent, thickener, opacifier, preservative, sequestering agent, antioxidant, perfume, agent for imparting pearlescence, colourant, pH modifier, reducing agent, electrolyte, oxidising agent, natural substance, anti-seborrhea agent, anti-grease agent, antidandruff agent or restructuring agent.

20. A composition according to claim 13, which is in the form of a shampoo, a lotion, gel or emulsion to be rinsed off before or after shampooing, before or after colouring or bleaching the hair or before or after perming, a styling or treatment lotion, a blow-drying or setting lotion, a hair lacquer or a composition for perming, colouring or bleaching the hair.

21. A composition according to claim 20 which is in the form of a shampoo and contains an anionic, non-ionic or amphoteric surface-active agent in an amount from 2 to 50% by weight.

22. A composition according to claim 20 which is in the form of a leave-on lotion and contains an anionic, non-ionic, cationic or amphoteric polymer in an amount of 0.1 to 10% by weight.

23. A composition according to claim 22 which contains 0.1 to 3% by weight of the said polymer.

24. A composition according to claim 20 which is in the form of a rinse-off lotion and contains, in aqueous, alcoholic or aqueous-alcoholic solution, at least one compound of the formula (I) and, optionally, from 0.1 to 10% by weight of a non-ionic or cationic surface-active agent.

25. A composition according to claim 20 which is in the form of a rinse-off non-ionic emulsion and contains at least one oil, fatty alcohol or polyoxyethyleneated fatty alcohol and water.

26. A composition according to claim 20 which is in the form of a rinse-off anionic emulsion and contains at least one soap.

27. A composition according to claim 20 which is in the form of a gel and contains 0.5 to 30% by weight of a thickener.

* * * * *